United States Patent [19]

Cromer, Jr. et al.

[11] Patent Number: 5,126,731
[45] Date of Patent: Jun. 30, 1992

[54] PNEUMATICALLY-CONTROLLED, USER-OPERATED SWITCH INTERFACE

[76] Inventors: Jerry E. Cromer, Jr.; Jerry E. Cromer, both of 119 McQueen St., Sumter, S.C. 29150

[21] Appl. No.: 539,682
[22] Filed: May 15, 1990
[51] Int. Cl.$^5$ .............................. B09G 3/00
[52] U.S. Cl. ..................... 340/825.19; 340/706; 340/709; 379/52; 341/21
[58] Field of Search .............. 340/825.19, 709, 706; 379/52; 434/112, 114; 400/87; 341/20, 21; 364/188, 238.2, 238.3, 239.9

[56] References Cited

U.S. PATENT DOCUMENTS

| | | |
|---|---|---|
| 3,229,059 | 1/1966 | Beatty . |
| 3,848,249 | 11/1974 | Meiri . |
| 3,911,316 | 10/1975 | Feick et al. . |
| 4,207,959 | 6/1980 | Youdin et al. . |
| 4,298,863 | 11/1981 | Natitus et al. . |
| 4,453,043 | 6/1984 | Zielinski et al. . |
| 4,562,432 | 12/1985 | Sremac ..................... 340/825.19 |
| 4,567,479 | 1/1986 | Boyd . |
| 4,706,067 | 11/1987 | Hauck ........................ 379/52 |
| 4,746,913 | 5/1988 | Volta ......................... 340/825.19 |
| 4,865,610 | 9/1989 | Muller . |
| 4,871,154 | 10/1989 | Seney . |
| 4,979,094 | 12/1990 | Gemmell et al. ............. 340/825.19 |

OTHER PUBLICATIONS

Proceedings of the Fourth Annual Conference on Systems and Devices for the Disabled, Jun. 1977 pp. 147-150.

U.S.A. Today-Techtalk "Physical Therapy and A Mean Pinball", Aug. 2, 1990.

*Primary Examiner*—Donald J. Yusko
*Assistant Examiner*—Peter S. Weissman
*Attorney, Agent, or Firm*—Oliff & Berridge

[57] ABSTRACT

A pneumatically-controlled, user-operated switch interface which allows a physically disabled person to operate electronic equipment such as a computer, television, video cassette recorder and a remote control includes apparatus providing at least one airway passage; first switching circuitry for producing a plurality of switching signals and having at least one pneumatic switch responsive to air pressure in the at least one airway passage; second switching circuitry settable in first and second switch positions for selectively connecting each of the plurality of switching signals to selected inputs of the electronic equipment as the electrical input signals, and user-activated apparatus for setting the second switching circuitry in the first and second switch positions. The switch interface can operate a plurality of computer input devices to allow a physically handicapped person to use commercially available software packages.

11 Claims, 11 Drawing Sheets

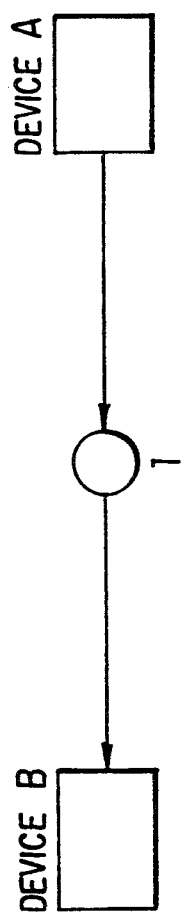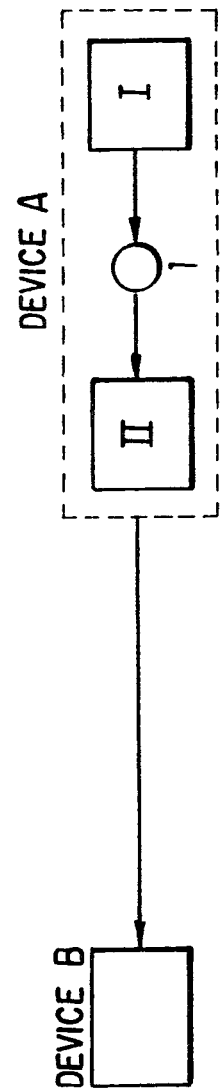
FIG. 1a
FIG. 1b

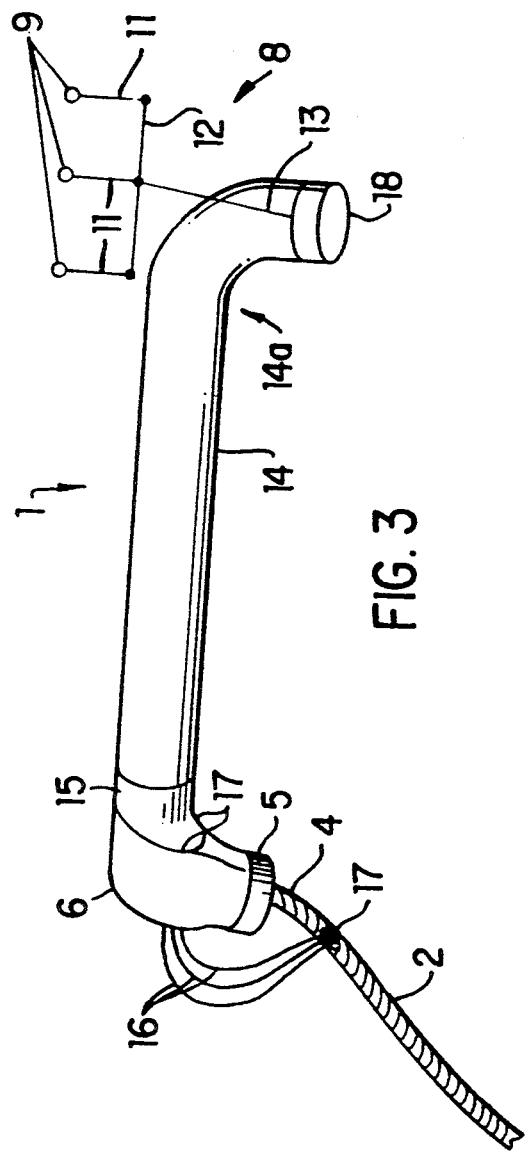
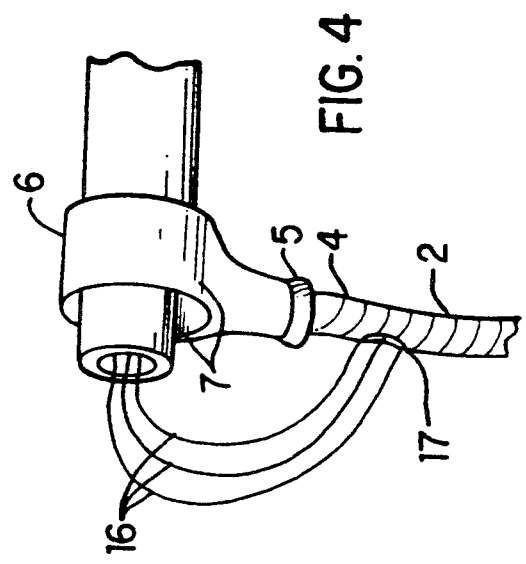

PNEUMATICALLY-CONTROLLED, USER-OPERATED SWITCH INTERFACE

BACKGROUND OF THE INVENTION

The invention relates in general to methods and apparatus for operator interfacing with electrical devices, and more particularly to a pneumatic switch interface which allows physically disabled people to interact with a computer.

Even the most routine tasks most people encounter in everyday life, including operating televisions, telephones, computers and other electronic equipment, become great challenges when attempted by a severely physically handicapped person. As a result, physically disabled persons are largely forced to be dependent on others to help them accomplish these basic needs.

Previously, substantial efforts have been devoted to the design of user-operated devices that permit the physically disabled to perform tasks by exploiting the abilities they do have. Thus, a number of devices have been developed which are adapted to be operated by extremities in which even severely physically handicapped people typically retain some degree of movement. One such device is disclosed in U.S. Pat. No. 3,229,059 to Beatty, which comprises a chin-operated switching controller that controls a television or radio when a person turns his head from side-to-side.

Although devices such as the Beatty controller allow handicapped persons to perform simple tasks, they are becoming increasingly disfavored due to their limited capability. Another approach is to use breath-controlled switches, which are especially helpful for the more severely physically handicapped persons, such as quadriplegics or bed-ridden patients. U.S. Pat. No. 4,298,863 to Natitus et al. discloses such a device wherein a bed-ridden patient blows on the pneumatic transducer of a portable patient call system to produce an alarm signal for calling a nurse. U.S. Pat. Nos. 3,848,249 to Meiri and 4,453,043 to Zielinski et al. disclose controllers for persons with motor impairments which automatically dial a telephone number when a person blows on a breath-operated microswitch. U.S. Pat. No. 4,207,959 to Youdin et al. discloses a voice-activated wheelchair controller with a plurality of breath-control tubes which override speech-activated control circuits to manually operate the movement of a motorized wheelchair. These devices help severely physically handicapped persons to perform various very simple tasks, but none are sophisticated enough to enable physically handicapped persons perform the complex tasks involved in operating a computer.

One computer input device that allows a physically impaired person to perform a limited number of functions on a computer is described in U.S. Pat. No. 4,567,479 to Boyd. The Boyd device comprises vacuum-operated switches which are controlled by a separate breath-control tube. Each switch generates when actuated a control signal that is connected directly into a computer which is controlled by a specially-modified software program. The control signal generated by each switch is associated with a different single operation to be performed by the computer as specified by the modified program. The Boyd input device is thus not adaptable to other computers or computer programs without creating new interface software and hardware specific to each computer and computer program. In addition, the Boyd input device is cranially mounted and operated, which may easily fatigue a physically disabled user after prolonged use. Further, because the Boyd input device is cranially operated, a user may require assistance from another when placing or removing such a device from his or her head.

SUMMARY OF THE INVENTION

An object of the present invention is to provide a pneumatically-controlled, user-operated switch interface that allows a user to operate a computer without special programming by sipping and puffing into breath-control tubes to generate control signals which replicate the operation of a peripheral computer input device.

Another object of the present invention is to provide a pneumatically-controlled, user-operated switch interface for electronic equipment which is switchable between different signal output modes to replicate the operation of a plurality of peripheral input devices.

It is yet a further object of the present invention to provide a pneumatically-actuated, user-operated switch interface for controlling signal input to electronic devices that performs a greater number of functions through an innovative multi-integrated design than permitted by known breath-actuated switch interfaces.

Another object of the present invention is to provide a compact, economical, non-fatiguing and easy to use electronic equipment input control system for use by persons who are severely physically disabled.

It is yet a further object of the present invention to provide an electronic equipment input control system for physically disabled users that is compatible with off-the-shelf peripheral input devices.

Still another object of the present invention to provide a stand-alone, breath-actuated switch interface which can be operated by a physically handicapped person and also by a non-physically disabled individual.

These and other objects are achieved by a pneumatically-controlled, user-activated switch interface for providing electrical input signals to an electronic device via a plurality of inputs of the electronic device, wherein the switch interface comprises apparatus providing at least one airway passage;

first switching circuitry for producing a plurality of switching signals and having at least one pneumatic switch responsive to air pressure in the at least one airway passage;

second switching circuitry settable in first and second switch positions for selectively connecting each of the plurality of switching signals to selected ones of the plurality of electronic device inputs as the electrical input signals, and user-activated apparatus for setting the second switching circuitry in the first and second switch positions.

BRIEF DESCRIPTION OF THE DRAWINGS

FIG. 1a is a block diagram showing a functional orientation of a pneumatic switch interface according to the invention.

FIG. 1b is a block diagram showing a second functional orientation of a pneumatic switch interface according to the invention.

FIG. 3 is a perspective view of a mouthpiece support unit suitable for use with the invention.

FIG. 4 is a perspective view of a holding piece suitable for use with the invention.

DETAILED DESCRIPTION OF THE PREFERRED EMBODIMENTS

Figure 2:
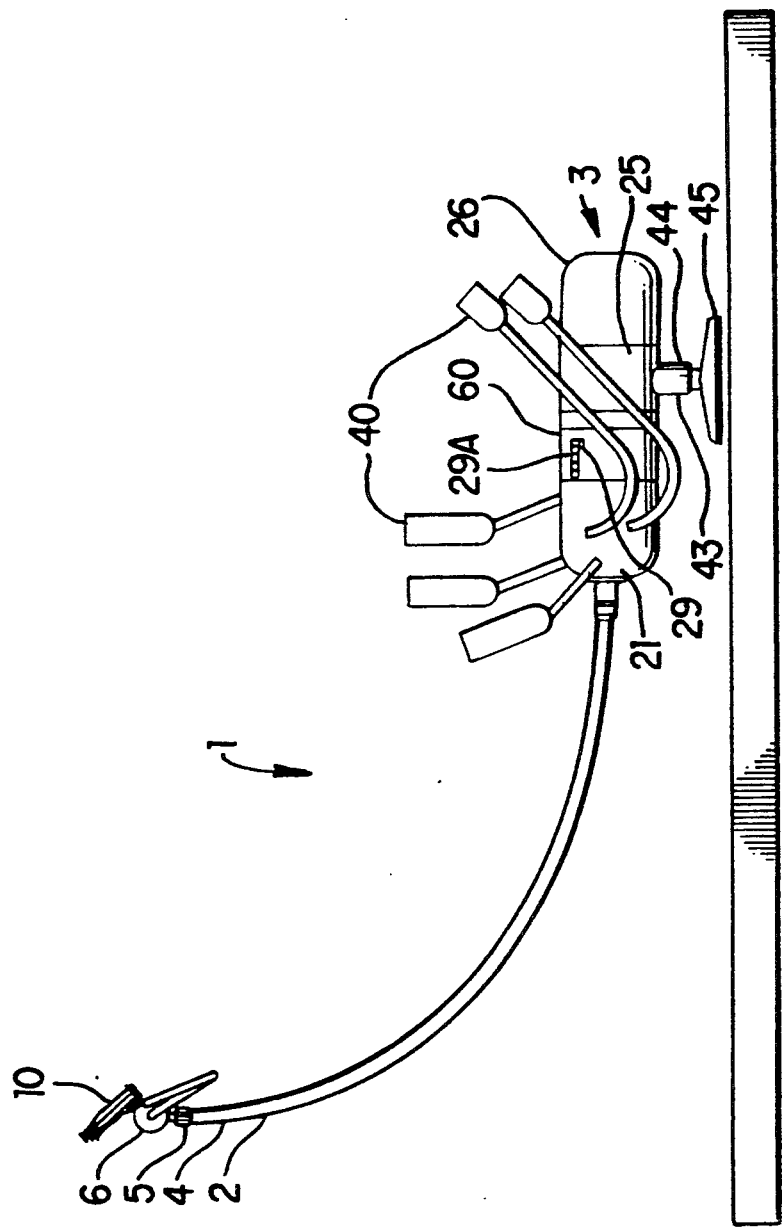
FIG. 2 is a perspective view of a pneumatic switch interface according to the invention.
Figure 5B:
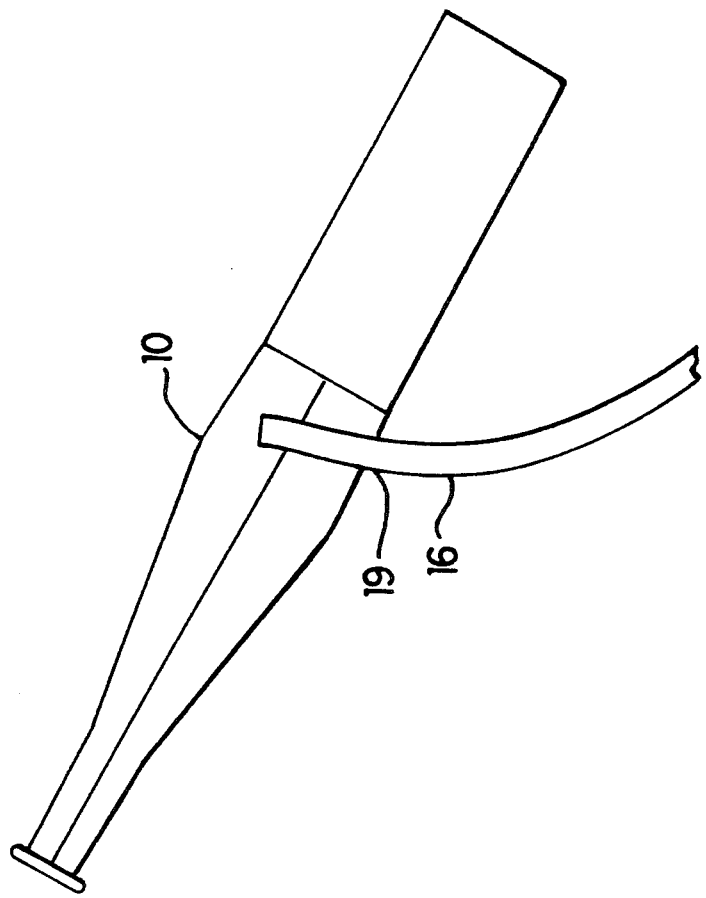
FIG. 5b is a diagram of an airway filtering system integrated into an integral mouthpiece unit suitable for use with the invention.
Figure 5A:
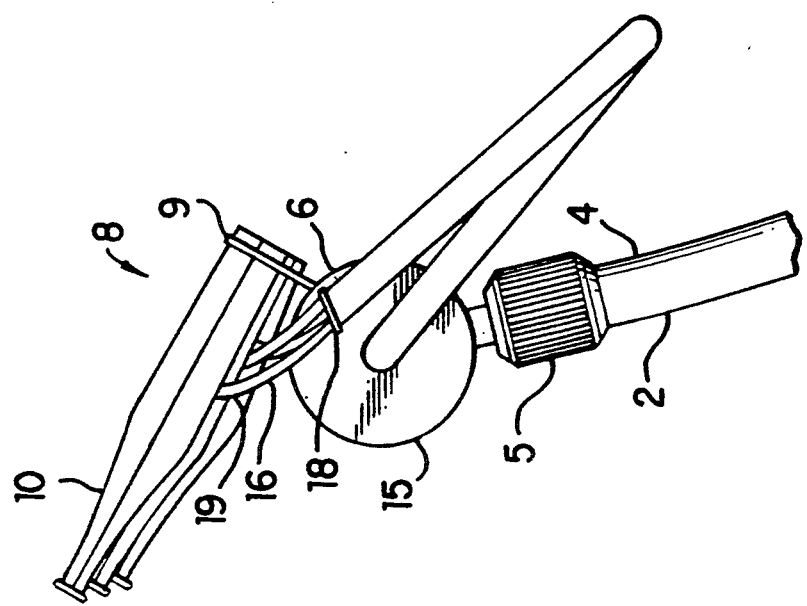
FIG. 5a is a more detailed perspective view of a mouthpiece support unit suitable for use with the invention.

The electronic device which is controlled by the pneumatically-controlled, user-activated switch interface of the present invention may be any device which receives electrical input signals from another device. Preferably, the signals are received via input wires or infrared electromagnetic radiation. Suitable electronic devices include computers and remote-controlled consumer electronic equipment such as televisions, video cassette recorders and stereos.

The pneumatically-controlled user-activated switch interface mimics the signals generated by a control device such as a computer input device, a video game controller or a television remote control. Typical computer input devices include a computer mouse, trackball, joystick, digitizing board, puck, and WIZ. Preferably, the switch interface contains circuitry which permits both conventional operation of the control device by a physically able individual, such as a care giver, and switch interface operation by a physically disabled individual when the care giver is unavailable.

"Physically disabled" and "physically handicapped" are used synonymously herein, and mean an individual who does not have adequate motor control to operate commercially available electronic control devices which are used by the general public in everyday life. It is believed the switch interface will find its greatest utility and advantage among physically disabled persons who possess sufficient control over at least one of their arms and hands to permit them to use the user-activated means for setting the second switching means in the first and second switch positions. More severely disabled persons may utilize the switch interface with the assistance of another individual, such as a care giver, to use the user-activated means for setting the second switching means in the first and second switch positions.

"High air pressure" means the higher than normal atmospheric air pressure produced by a person puffing or blowing into an airway passage. "Low air pressure" means the lower than normal atmospheric air pressure produced by a person sucking or sipping into an airway passage.

The means for providing at least one airway passage may be any airtight passage which can conduct high and low air pressure from one end of the passage to the other. The airtight passage must be sufficiently strong not to burst under high air pressure and sufficiently rigid not to collapse under low air pressure. Preferably, the airtight passage is a flexible tube. Most preferably, the means for providing at least one airway passage include at least 3 separate flexible tubes, each made from an air impermeable plastic.

One end of the airway passage communicates with the first switching means. The opposite end of the airway passage receives high and low air pressure from the user's mouth. Preferably, this is facilitated by means of a mouthpiece which is detachably attached to the opposite end of the airway passage.

The first switching means for producing switching signals comprises at least one pneumatic switch responsive to the air pressure in the airway passage. Preferably, the first switching means will generate a first switching signal when there is high air pressure within the airway passage and a second switching signal when there is low pressure within the airway passage. A particularly preferred embodiment comprises a low-pressure responsive switch and a high-pressure responsive switch, each in airtight parallel communication with the airway passage, such that the air pressure within the airway passage is simultaneously applied to each switch. In a still more preferred embodiment, the first switching means comprise a plurality of such pairs of vacuum-actuated and pressure-activated switches, with each pair in separate communication with a separate airway passage.

The second switching means comprises any means which is settable in first and second switch positions so as to selectively connect the switching signal generated by the first switching means to selected inputs of an electronic device. The second switching means are settable in the first and second switch positions by user-activated means, which may be any means which may be used to set the second switching means in its first and second switch positions. A rotatable switch incorporated into a housing of the switch interface, push buttons and slide switches are three preferred user-activated means for setting the second switching means. A particularly preferred embodiment includes at least one electrical switch exposed through an upper housing cap of the switch interface housing.

The interface switch preferably includes a housing which may be preferably rotatably mounted upon a surface. The mounting includes securing means which preferably includes clamps, suction cups, screws or grips.

The operation of the above-described pneumatically-controlled, user-operated switch interface may be briefly described as follows: The physically disabled user, or his or her care giver, turns on the electronic equipment which is desired to be used and manually selects either the first or second switch positions on the switch interface using the user-activated means for setting the second switching means, thus setting the switch interface to provide electrical signals which comprise input signals to the specific electronic equipment which is desired to be used. The physically disabled user may then control the operation of the electronic device by selectively puffing or sipping into the air passage, thereby creating electrical signals in the first switching means which are applied to the inputs of the electronic device through the second switching means. When the user desires to utilize the switch interface for a different electronic device, or a different electronic function of the same device, the user, or his or her care giver, simply employs the user-activated means for setting the second switching means to select the other switch position, thereby altering the inputs applied to the electronic device. Thus, the pneumatically-controlled, user-activated switch interface of the present invention may be employed by a physically disabled user to control more than one electronic device or more than one function of a complex electronic device.

The general theory of operation of the present invention is illustrated in FIGS. 1a and 1b. Referring to FIG. 1a, a pneumatically-controlled, user-operated switch interface 1 in accordance with the invention is interposed between two electronic devices A and B. In general, the control signal output of device A controls the operation of device B. Typically, device A is an input device such as a computer mouse or joystick having manual switch buttons which, when pushed by a physically able person, control a computer program on the computer of device B. Switch interface 1 is wired in parallel with device A so that either device A or switch interface 1 may control the operation of device B. In this particular case, switch interface 1 replicates the operation of the mouse or joystick by reproducing the n-bit instruction word that is transmitted from device A into device B.

FIG. 1b shows pneumatically-controlled, user-operated switch interface 1 in a similar but slightly different configuration in which switch interface 1 is interposed between components I and II of device A for generating a signal output for controlling device B. Typically, component I may be a computer puck having manual switch buttons which communicates with the digitizing tablet of component II for collectively controlling the operation of device B by a physically able person. Switch interface 1 is wired in parallel with the puck, thereby replicating the puck's signal output.

Referring to FIGS. 2 and 3, a pneumatically-controlled switch interface 1 comprises a flexible tube 2 extending from a main body 3 to distal end 4. The distal end 4 of flexible tube 2 screws into threaded cap 5 of holding piece 6. Holding piece 6 has a pair of jaws 7 which hold a mouthpiece support unit 8.

Main body 3 can be secured in a vertical position during switch interface operation, for example, by a suction cup that is attached to a lower housing cap 26 that grips the surface of a floor or desk top, or by a C-clamp that attaches around the circumference of a switch housing 25 of the main body 3 and screws onto a jutting table edge or the like.

Switch housing 25 may be mounted horizontally on a table top as shown in FIG. 2. In this configuration, the main body 3 is mounted onto a short section of PVC tubing 43 in a swivel rigid mount connection. The threaded end 44 of the section of PVC tubing screws into a mounting plate 45 attached onto the surface of a table. The swivel action of main body 3 provides an added degree of freedom to a handicapped user. For instance, by gripping mouthpieces 10 with his or her teeth, a user may rotate the mouthpiece support unit 8 into a working position or may push the unit aside when a session is complete.

As shown in FIG. 3, the bottom of each support ring 9 fastens to mounting stem 11 which serves to position the associated mouthpiece 10 for use by a physically disabled user. Stems 11 are mounted side-by-side in closely spaced planar relationship on short horizontal support bar 12 to allow ready access to any mouthpiece 10 without substantial effort by the user. Horizontal support bar 12 is mounted on one end of elongated tube 14 by support rod 13. Elongated tube 14 has a hooked distal end section 14a for locating the array of mouthpieces in a more accessible position for the user. The other end of elongated tube 14 extends into and frictionally engages the inner surface of a short, conically-shaped hollow support member 15.

Jaws 7 of the holding piece 6 grip the outer surface of hollow support member 15 to effectively support the mouthpiece support unit 8 in place. The hollow support member 14 rotates within jaws 7 to position the array of mouthpieces in different positions to accommodate the needs of each individual user.

Referring to FIGS. 3, 4, 5a and 5b, mouthpiece support unit 8 includes an array of support rings 9, each of which frictionally holds a mouthpiece 10. Each mouthpiece 10 preferably has an internal wet cotton filter, for example as disclosed in U.S. Pat. No. 4,046,153, which collects saliva and entraps harmful bacteria during use of switch interface 1. The array is replaceable to maintain proper sanitation between multiple users.

A plurality of air lines 16 are enclosed within the interior of flexible tube 2. Air lines 16 exit flexible tube 2 through hole 18 and extend into support member 15. At the open end 18 of elongated tube 14, air lines 16 separate, with each line extending into a hole 19 in the underside of a respective one of the mouthpieces 10. Air lines 16 are held in frictional contact with each hole 19 in an airtight connection.

To prevent damage to air lines 16 that might occur as a result of crimping or twisting, a stainless steel spring or rigid reinforcing wire (not shown) may be fixed on the exterior surface of flexible tubing 2. Alternatively, each flexible tube 2 may be made from a protective ribbed metal tubing, such as the type of tubing used to sheath the receiver coils on a public telephone, that is durable enough to withstand normal every-day use. Flexible tube 2 is sufficiently long and flexible to assume any orientation required to position mouthpieces 10 for comfortable use by a physically handicapped user.

Figure 6:
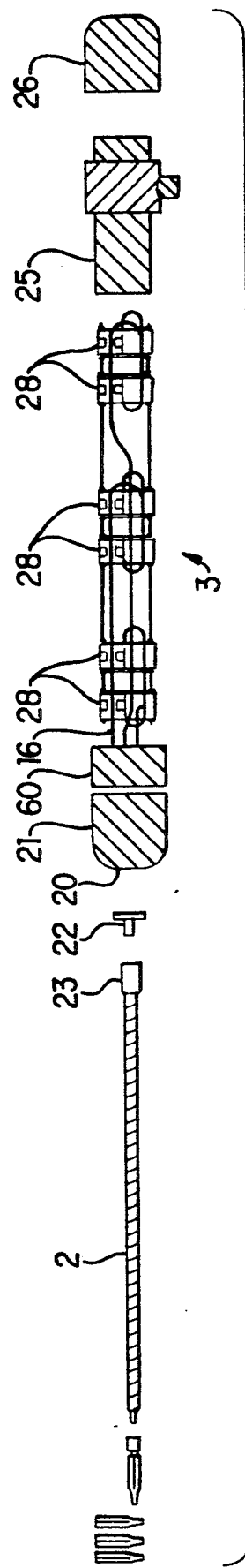
FIG. 6 is an internal view of the switch housing of the switch interface of FIG. 1.

Flexible tube 2 extends into main body 3 via opening 20 in upper housing cap 21, as shown in FIG. 6. Flexible tube 2 attaches to upper housing cap 21 by via threaded flange 22 which mates with connector attachment 23 on flexible tube 2. Each of the three air lines 16 are respectively connected to a first switching means which are mounted within switch housing 25 of main body 3. The second switching means is retained in rotatable housing portion 60 which is mounted between switch housing 25 and upper housing cap 21. The switch housing 25 may be made from PVC tubing that is secured to upper housing cap 21, via rotatable housing portion 60, and a lower housing cap 26 by screws (not shown) to form an enclosure around the first switching means.

Specifically for the case where device B is a computer, as illustrated in FIG. 1a, pneumatically-controlled switch interface 1 generates a signal output which replicates the signal output of a selected peripheral computer input device A. The first switching means comprise arrays of pneumatic switch assemblies 28. The second switching means comprise a group of external manual selector switches 29. The array of pneumatic first switch assemblies 28 cooperates with the group of second switching means 29 to complete an electrical circuit for placing signal voltages onto the correct leads of a computer pin-plug interface for replicating the operation of an input device, based on the high and low air pressure exerted upon the pneumatic switch assemblies by the user.

Figure 7:
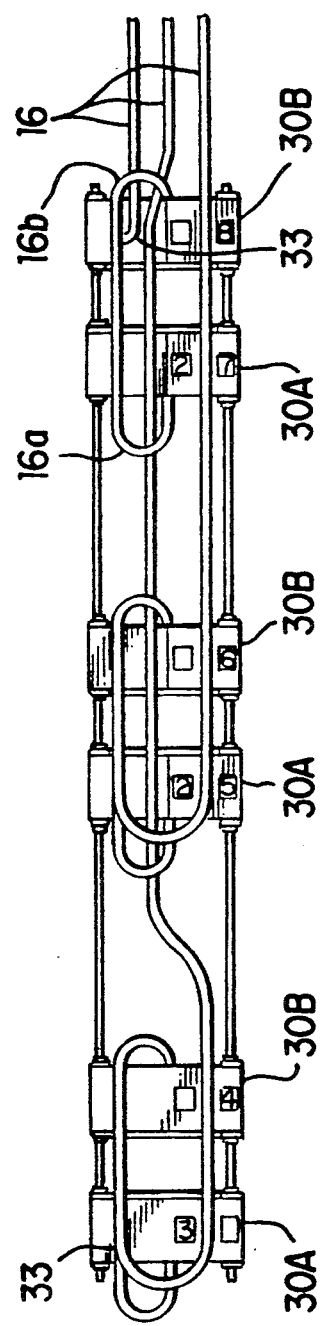
FIG. 7 is a diagram of the control circuitry within the switch housing of the present invention.

As shown in FIG. 7, each switch assembly 28 comprises associated vacuum and pressure sensitive micropneumatic switches 30A and 30B which produce switching signals in response to high and low air pressure created within an airline 16 by a user sipping or puffing onto a mouthpiece 10. Micropneumatic switches 30A and 30B are commercially available, i.e. Micropneumatic Logic Industry, Part #502-P-G-RANGE-A. Second switching means 29 selectively connect switching signals generated by the pneumatic first switching means 28 onto the correct pins of an 8-pin computer plug to produce a signal output that is compatible with a selected computer input device. It will be appreciated that first switching means (switch assemblies 28) and second switching means (selector switches 29) can be implemented using printed circuit board or integrated circuit technology in lieu of discrete components.

Within switch housing 25, each air line 16 splits into two separate air lines 16a and 16b via a Y-shaped connector 33. Air lines 16a and 16b are connected to the associated vacuum switch 30A and the pressure switch 30B, respectively, so that the air pressure within each air line 16 is applied to both of its associated switches 30 simultaneously.

During operation of switch interface 1, a puff of air on a mouthpiece 10 causes high air pressure within an associated air line 16 that is simultaneously applied to both an associated vacuum switch 30A and pressure switch 30B via communicating air line branches 16a and 16b. The high air pressure closes pressure switch 30B to generate a corresponding first signal output while the vacuum switch 30A remains inactive. Analogously, low air pressure caused by a sip through airline 16 closes a vacuum switch 30A to produce a corresponding second signal output while the pressure switch 30B remains inactive. Therefore, each airline 16 has the capability of specifying two independent functions that can be performed on a computer.

Closing the pneumatic first switching means creates switching signals which are selectively directed onto the correct pin configuration by the second switching means (external selector switches 29) for replicating the signal output of a desired peripheral computer input device.

By adding air lines and associated switching circuitry, switch interface 1 may be expanded to specify more functions. For example, a switch interface having two air lines is able to implement four functions, a switch interface having three air lines is able to implement six functions, and so on.

Figure 8:
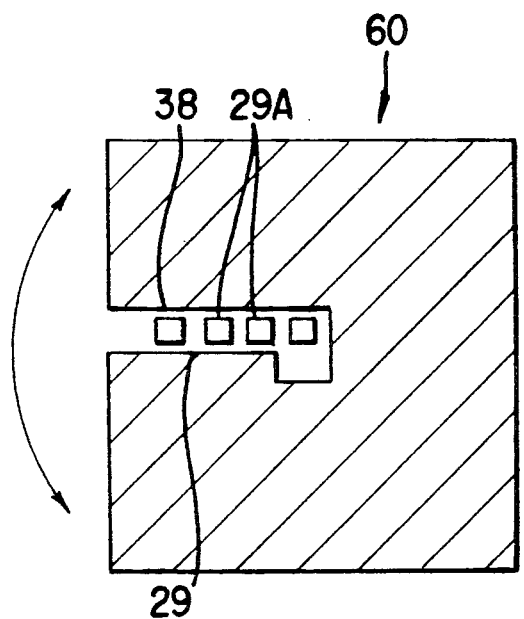
FIG. 8 is a diagram of the user-activated means for setting the second switching means of the switch interface of the present invention.

Referring to FIG. 8, the second switching means are mounted so that four operator actuator members 29A thereof extend through hole 38 in rotatable housing portion 60. By varying the orientation of operator actuator members 29A between two switching configurations, the pneumatically-controlled switch interface can produce a signal output which replicates the signal output of a selected computer input device. Rotation of housing portion 60 so that rotatable housing portion 60 engages three of the four selector members 29A causes the selector members 29A to move into a second configuration. The fourth switch must be manually switched from one position to a second position. Switching configuration I produces a signal output which is compatible with a first class of input devices. Alternatively, switching configuration II produces a signal output which is compatible with a second group of input devices.

Once a physically disabled user sips or puffs on a mouthpiece 10 to select a desired function on the computer, switch interface 1 replicates the signals produced by a selected input device by placing signal voltages on those leads which correspond to a specific input pin configuration. The signals pass from the switch housing along these leads into the computer serial input port for processing by the associated computer input device software. By selectively connecting signal voltages onto the correct pins of a computer plug interface, switch interface 1 can replicate the operation of various input devices.

Input devices may be integrated onto the switch interface 1 by connecting the jack on an input device cable to its female counterpart 40 on an external cable that extends from switch housing 25. By the same token the switch interface 1 may employ an external cable to carry signals out from the switch housing for processing.

Figure 9:
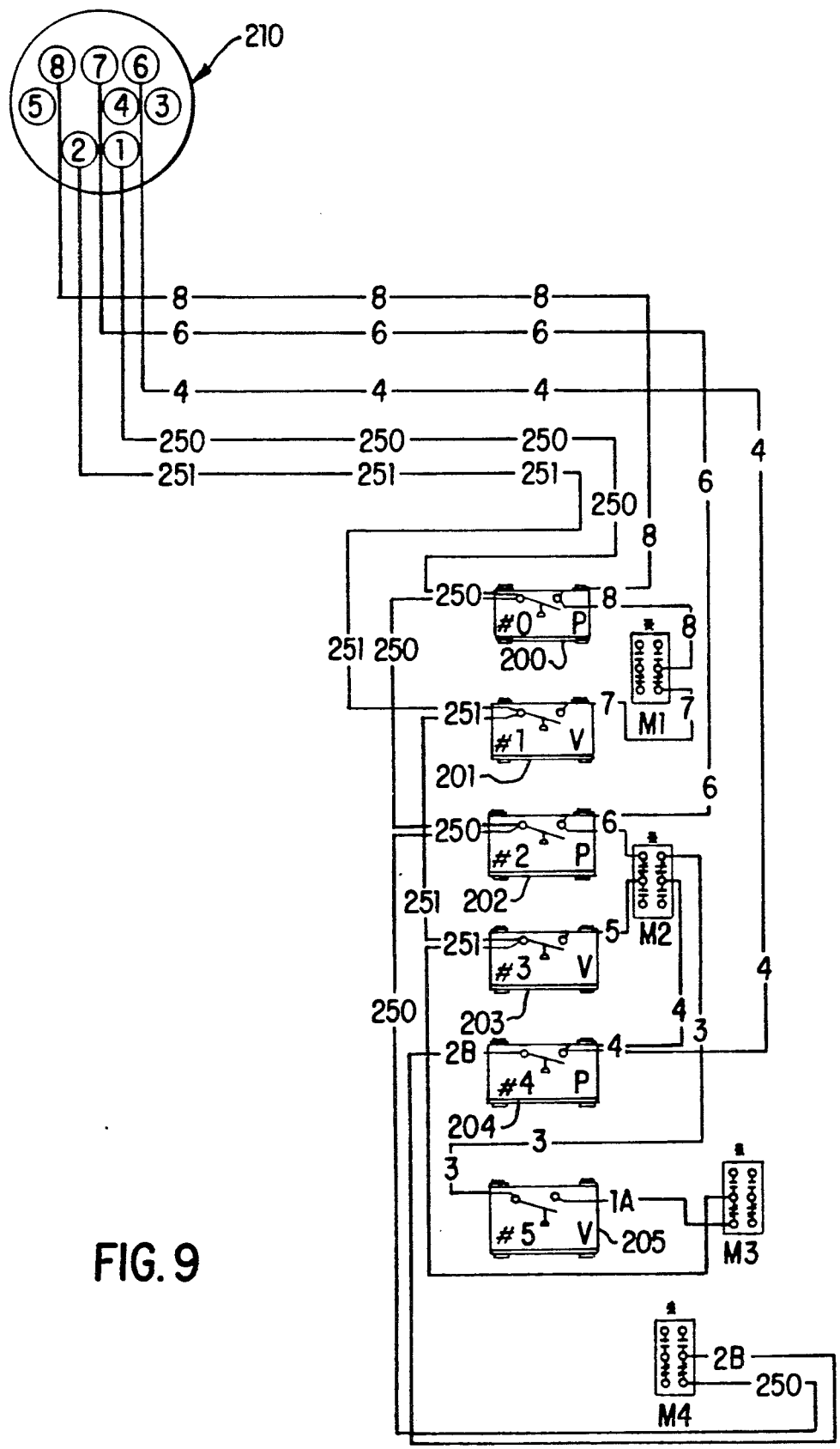
FIG. 9 is a circuit diagram for a switch interface of the invention configured for a digitizer for use with a computer mouse.
Figure 10:
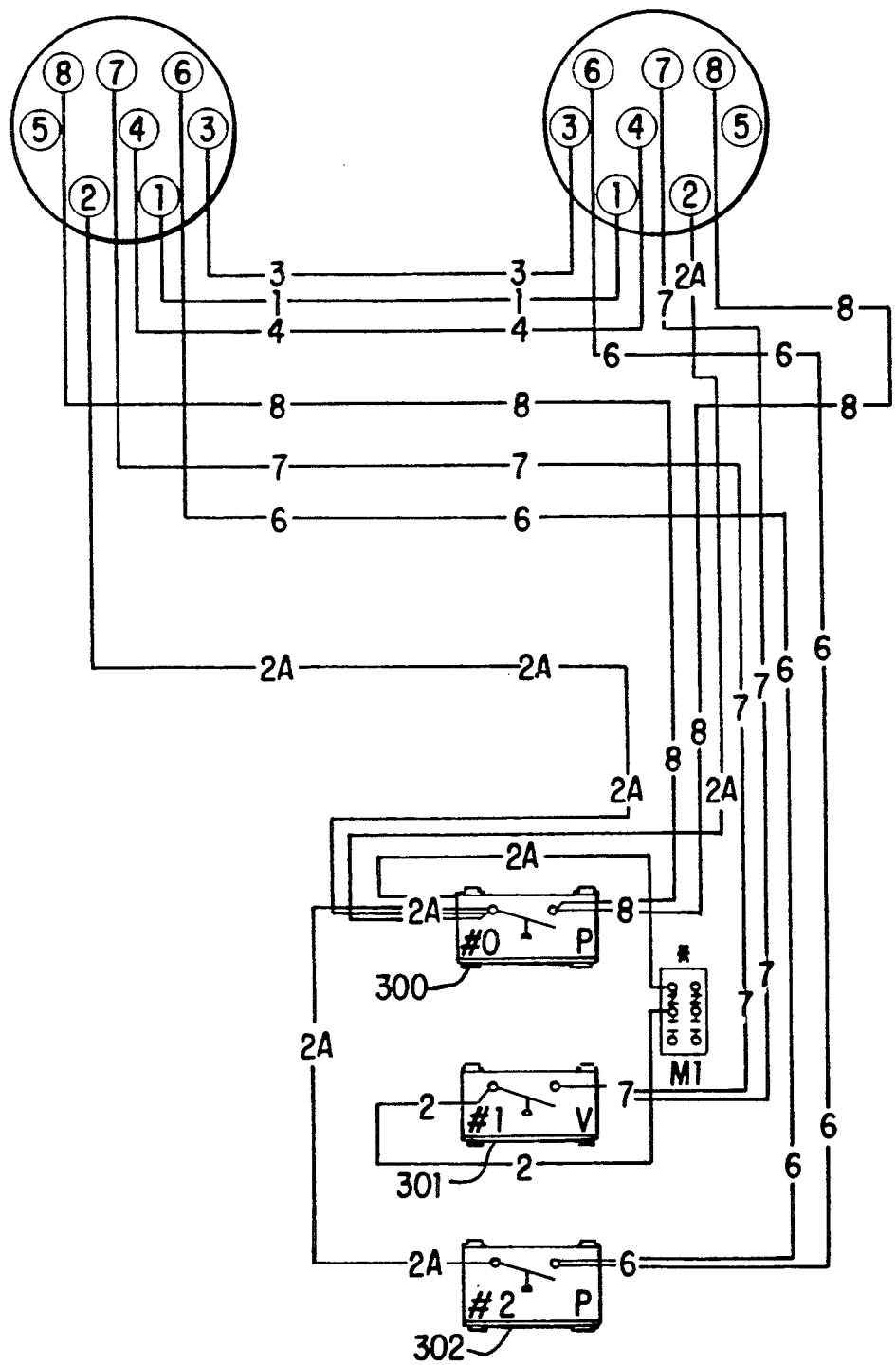
FIG. 10 is a circuit diagram for a switch interface of the present invention configured for a computer mouse.
Figure 11:
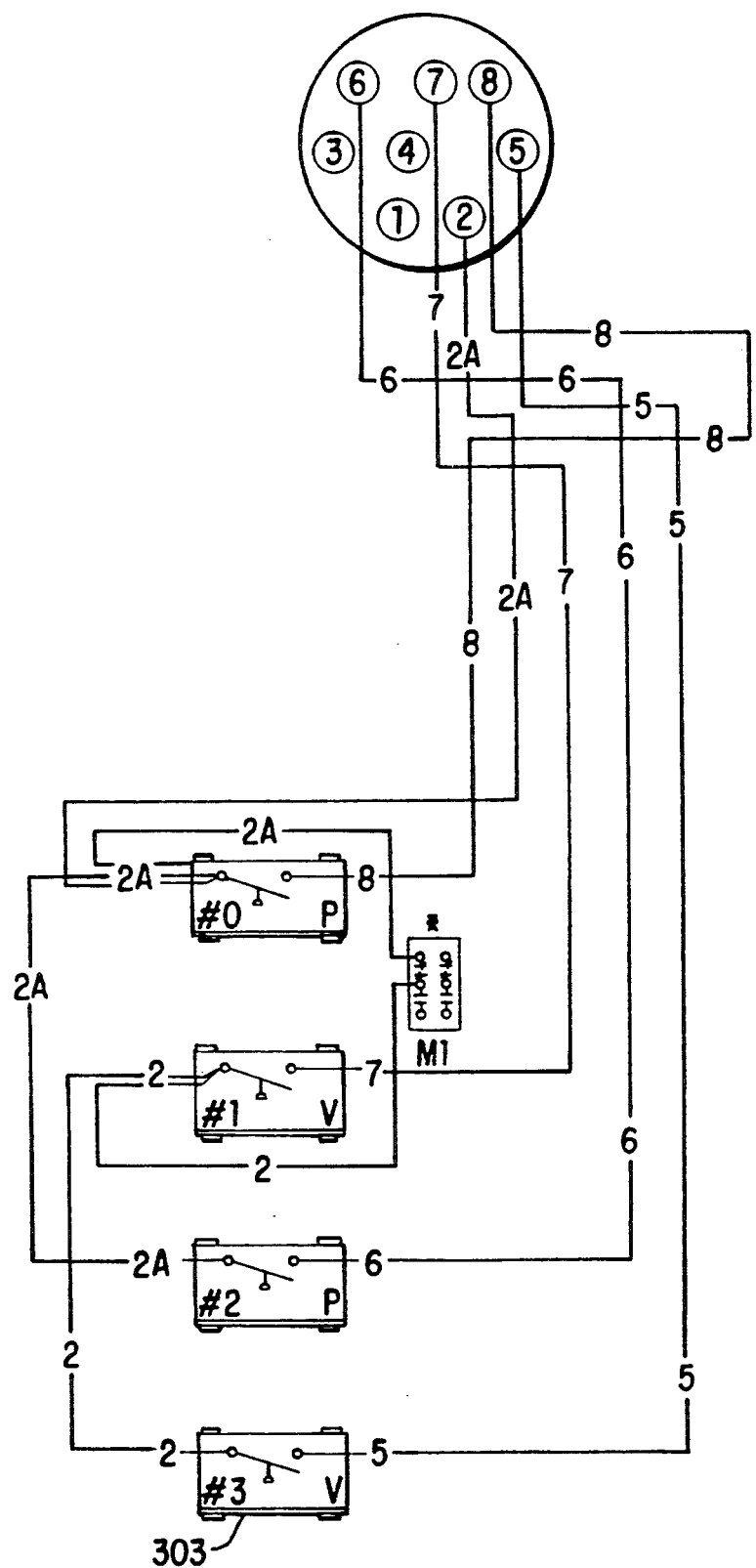
FIG. 11 is a circuit diagram for a switch interface of the present invention configured for a computer joystick.
Figure 12:
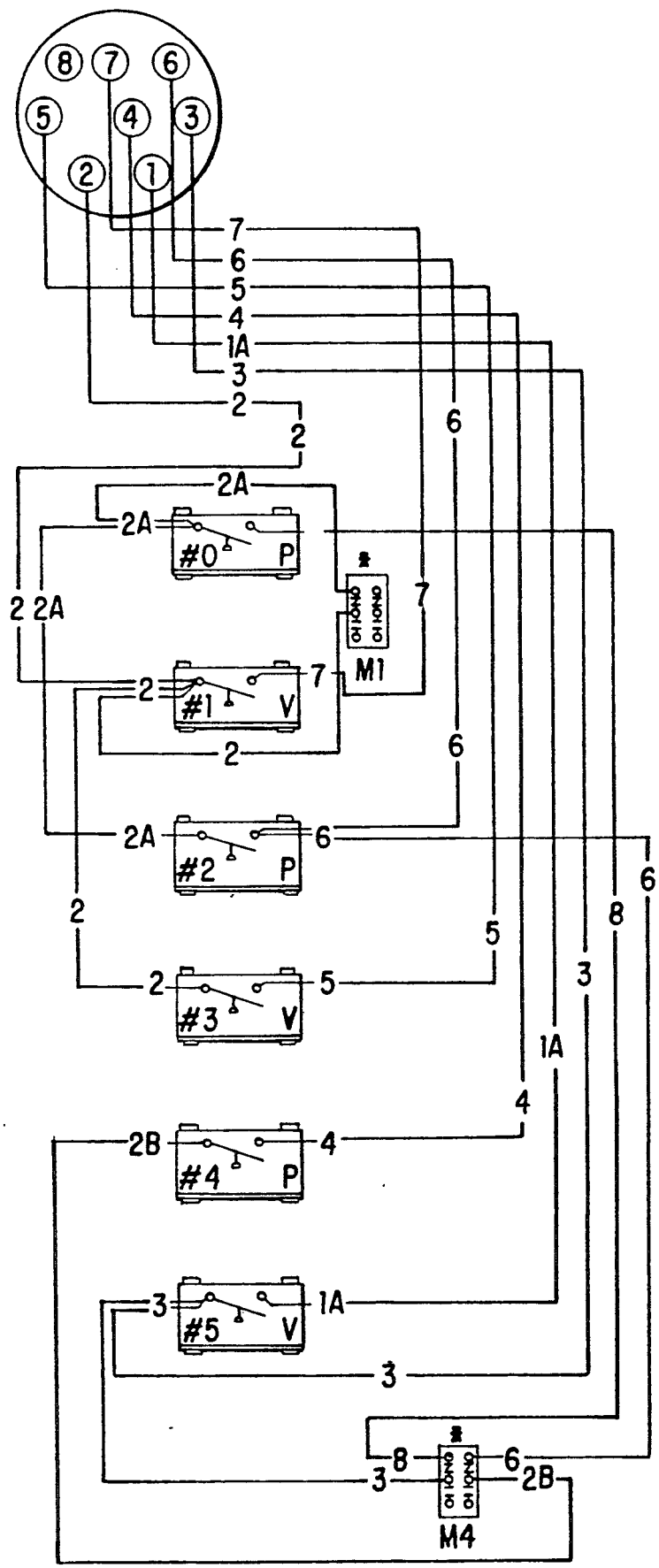
FIG. 12 is a circuit diagram for a switch interface of the present invention configured for a hand-held remote control for a television.

FIG. 9 shows a practical example of how switch interface 1 replicates the operation of one class of input devices when second switching means 29 are moved into first switching configuration. FIGS. 10–12 show practical examples of how switch interface 1 can replicate the operation of a second class of input devices when second switching means 29 are moved into a second switching configuration.

The circuit diagram of a pneumatically controlled, user-activated switch interface for replicating the signal output of a CALCOMP Model 33110 WIZ computer input device is shown in FIG. 9. The WIZ is a computer input device comprising a puck with six manual switch buttons which select functions on a digitizing board for implementing functions on a computer. Pneumatically-controlled switch interface 1 uses its first switching means to generate switching signals for replicating the signal generated by pushing each manual switch button. By manually placing selector switch M1 in the configuration shown, switch interface 1 generates switching signals from its first switching means 200–205 which reproduce the puck's manual switch button signals. The three air pressure-actuated switches 200, 202 and 204 and the three vacuum-actuated switches 201, 203 and 205 individually close to complete specific circuit paths which selectively connect signal voltages to output leads 6, 7 or 8 of pin-plug 210 on the digitizing board. The pneumatically-controlled first switching means of switch interface 1 is connected in parallel to corresponding leads from the WIZ input device so that it retains full operational capability in lieu of signals directed through switch interface 1.

Pneumatically-controlled first switching means 200–205 individually close for generating a 4-pin signal for performing one of six distinct computer functions. Pins 1 and 2 carry source voltage from the digitizing board's power supply (not shown) to pneumatically-controlled first switching means 200–205. For example, pin 2 may carry a +5 V dc signal to vacuum-actuated switches 201,203,205. Accordingly, pin 1 carries −5 V dc to pressure-actuated switches 200,202,204. If +5 V dc is considered high (H) and −5 V is considered low (L), the following Table I represents the 6-line signal generated by pneumatically-controlled first switching means 200–205 across pins 6, 7 and 8 of an 8-pin computer serial port for performing 6 separate functions:

TABLE 1

| \multicolumn{3}{c}{Pins} | |
|---|---|---|---|
| 6 | 7 | 8 | Computer functions |
| — | — | L | function 1 |
| — | — | H | function 2 |
| — | L | — | function 3 |
| — | H | — | function 4 |
| L | — | — | function 5 |
| H | — | — | function 6 |

Specifically, when pneumatic switch 200 closes, which would be analogous to pressing a manual switch button on the WIZ's puck, −5 V dc is selectively connected from pin 1 along lead 250 to pin 8, making pin 8 go low. Similarly, when switch 201 closes, +5 V dc is selectively connected from pin 2 along lead 251 to pin 8 through selector switch M1, making pin 8 go high. This would correspond to closing a second manual switch on the WIZ puck. Analogously, when switch 202 closes, +5 V dc is selectively connected to pin 7, making it high. When switch 203 closes, −5 V dc is selectively connected to pin 7 through selector switch M2, making it low. And, when switches 204 and 205 close, −5 V dc and +5 V dc are placed on pin 6, respectively, making it low and high in each case. Selector switches M3 and M4 selectively connect source voltages from pins 1 and 2 to switches 204 and 205, respectively. Pins 3, 4 and 5 are inoperative in this illustrative embodiment.

For the second selector switch configuration, the circuit diagrams of switch interface 1 for replicating the push of buttons on a computer mouse, joystick, and a remote control are shown. A computer mouse typically has several buttons which, when pushed, control different functions on a computer. FIG. 10 shows the circuit diagram for switch interface 1 for a GENIUS Model GM-6 mouse. In this configuration, three pneumatically-controlled first switching means 300, 301 and 302 generate switching signals which correspond to each of three manual switches on the mouse. The switching signals form a 3-bit digital signal which is selectively placed onto pins 6, 7 and 8 for input into the computer when certain pneumatic switches are closed. Selector switch M1 connects source voltage from pin 2 to switch 301. Pins 1, 3 and 4 bypass all associated pneumatic circuitry to carry mouse positional signals to the computer. Pin 5 is inoperative in this illustrative example. The following Table 2 defines the 3-bit digital code generated by switch interface 1 for emulating the operation of the mouse.

TABLE 2

| \multicolumn{3}{c}{Pins} | |
|---|---|---|---|
| 6 | 7 | 8 | Mouse functions |
| 0 | 0 | 1 | switch 1 |
| 0 | 1 | 0 | switch 2 |
| 1 | 0 | 0 | switch 3 |

FIG. 11 shows the circuit diagram for the switch interface 1 corresponding to a CALCOMP Model 23120 puck and digitizing board computer input device. In this configuration, an additional pneumatically-controlled switch 303 is added to the first switching means circuitry of FIG. 10. Pneumatic switching signals generate a 4-bit digital code that corresponds to each of four buttons on the puck. Selector switch M1 connects source voltage from pin 2 to the vacuum-actuated pneumatic switches. Pins 1, 3 and 4 carry positional signals directly from the puck to the digitizing board bypassing all pneumatic circuitry. The following Table 3 defines 4-bit digital signal generated by switch interface 1 for replicating the operation of the puck.

TABLE 3

| \multicolumn{4}{c}{Pins} | |
|---|---|---|---|---|
| 5 | 6 | 7 | 8 | Computer functions |
| 1 | 0 | 0 | 0 | function 1 |
| 0 | 1 | 0 | 0 | function 2 |
| 0 | 0 | 1 | 0 | function 3 |
| 0 | 0 | 0 | 1 | function 4 |

FIG. 12 shows the circuit diagram for a pneumatically-controlled, user-operated switch interface corresponding to a Curtis Mathis hand-held remote controller for a television set. In this configuration, additional pneumatically-controlled switches are added for performing six different television functions. By puffing or sipping into the appropriate air line, a user may be able to turn a television on or off, increase or decrease volume, and change the channel. Pin 8 is inoperative in this illustrative embodiment.

The pneumatically-controlled, user-operated switch interface of the present invention may be used to operate any number of input devices, to provide a physically disabled person the ability to operate complicated drawing programs, such as AutoCAD, or video games, such as NINTENDO.

Those of ordinary skill in this art will understand that the above-described embodiments are merely illustrative examples of the invention application. Numerous other arrangements may be readily devised by those skilled in the art which will embody the principles of the invention and fall within the spirit and scope of the appended claims.

I claim:
1. A pneumatically-controlled, user-actuated, switch interface for providing electrical input signals to an electronic device via a plurality of inputs of said electronic device, said switch interface comprising:
 means for providing at least one airway passage;
 first switching means for producing a plurality of switching signals having at least one pneumatic switch responsive to air pressure in said at least one airway passage;
 second switching means settable in first and second switch positions for selectively connecting each of said plurality of switching signals to selected ones of said plurality of electronic device inputs as said electrical input signals; and
 user-activated means for setting said second switching means in said first and second switch positions.

2. The switch interface of claim 1, wherein said second switching means comprises a plurality of switches interconnected between said at least one pneumatic switch and said electronic device inputs, and said setting means comprises rotatable switch housing means for urging said plurality of switches between said first and second switch positions when rotated.

3. The switch interface of claim 1, wherein the electronic device is selected from the group consisting of a computer, a video game, a television, a video cassette recorder and a stereo.

4. The switch interface of claim 1, wherein said first switching means comprises a plurality of pairs of low air pressure-actuated and high air pressure-actuated switches.

5. The switch interface of claim 1, wherein said user-activated means for setting said second switching means includes at least one electrical switch exposed through an upper housing cap.

6. The switch interface of claim 1, wherein said input device retains full operational capability.

7. The switch interface of claim 1, wherein said first switching means is capable of generating two distinct electrical input signals per each airway passage.

8. The switch interface of claim 1, further comprising a housing and means for rotatably mounting said housing.

9. The switch interface of claim 8, wherein the mounting means includes means for securing said housing to a surface.

10. The switch interface of claim 9, wherein the securing means is selected from the group consisting of clamps, suction cups, screws and grips.

11. A user-actuated, pneumatically-controlled switch interface as specified in claim 1, wherein said electronic device is selected from the group consisting of a mouse, joystick, trackball, digitizing board, puck, and a remote control.

* * * * *

UNITED STATES PATENT AND TRADEMARK OFFICE
CERTIFICATE OF CORRECTION

PATENT NO. : 5,126,731

DATED : June 30, 1992

INVENTOR(S) : Jerry E. CROMER, Jr. and Jerry E. CROMER

It is certified that error appears in the above-identified patent and that said Letters Patent is hereby corrected as shown below:

On the title page, section [22], the filing date, is changed from "May 15, 1990" to --June 15, 1990--.

Signed and Sealed this

Third Day of August, 1993

Attest:

MICHAEL K. KIRK

*Attesting Officer*   Acting Commissioner of Patents and Trademarks